US005653235A

United States Patent [19]
Teo

[11] Patent Number: 5,653,235
[45] Date of Patent: Aug. 5, 1997

[54] SPECKLE REDUCTION IN ULTRASOUND IMAGING

[75] Inventor: Tat-Jin Teo, Redmond, Wash.

[73] Assignee: Siemens Medical Systems, Inc., Iselin, N.J.

[21] Appl. No.: 576,535

[22] Filed: Dec. 21, 1995

[51] Int. Cl.$^6$ .................................................. A61B 8/00
[52] U.S. Cl. ................................ 128/661.01; 73/626
[58] Field of Search .................. 128/660.01, 660.07, 128/661.01, 661.09; 73/626; 382/128, 254, 264, 266, 274

[56] References Cited

U.S. PATENT DOCUMENTS

| | | | |
|---|---|---|---|
| 4,886,069 | 12/1989 | O'Donnell | 128/661.01 |
| 4,890,268 | 12/1989 | Smith et al. | 367/138 |
| 4,949,310 | 8/1990 | Smith et al. | 367/7 |
| 5,329,930 | 7/1994 | Thomas, III et al. | 128/661.01 |
| 5,394,151 | 2/1995 | Knaell et al. | 342/25 |
| 5,479,926 | 1/1996 | Ustuner et al. | 128/660.04 |
| 5,483,963 | 1/1996 | Butler et al. | 128/661.01 |
| 5,546,946 | 8/1996 | Souquet | 128/662.03 |

OTHER PUBLICATIONS

Jeffrey J. Giesey et al., "*Speckle Reduction in Pulse-Echo Ultrasonic Imaging Using A Two-Dimensional Receiving Array,*" IEEE Transactions on Ultrasonics, Ferroelectrics, and Frequency Control, vol. 39, No. 2, Mar. 1992.

P. Mohana Shankar et al.: "Speckle Reduction with Improved Resolution in Ultrasound Images," IEEE Transactions on Sonics and Ultrasonics, vol. SU–32, No.4, Jul. 1985.

Gregg E. Trahey et al.: "Speckle Pattern Correlation with Lateral Aperture Translation: Experimental Results and Implications for Spatial Compounding," IEEE Transactions on Ultrasonics, Ferroelectrics, and Frequency Control, vol. UFFC–33, No. 3, May 1986.

S.D. Silverstein: "Coherence and speckle reduction in compounded correlated phased arrays: synthetic aperture radar," Journal of the Optical Society of America, vol. 3, No. 11, Nov. 1986.

Nihat M. Bilgutay et al.: "Spatial processing for coherent noise reduction in ultrasonic imaging," Journal of the Acoustic Society of America, 87 (2), Feb. 1990.

Turnbull, et al.: "Beam Steering with Pulsed Two–Dimensional Transducer Arrays," IEEE Transactions on Ultrasonics, Ferroelectrics, and Frequency Control, vol. 38, No. 4, Jul. 1991.

*Primary Examiner*—Francis Jaworski

[57] ABSTRACT

A system and a method for generating an ultrasound image of an interrogation region in an object with a transducer with a two-dimensional array of transducer elements, includes the steps of generating an ultrasound beam by activating many transducer elements of the two-dimensional array; electronically controlling the beam to illuminate substantially the same region from at least two orientations; capturing the echoes generated with the beam illuminating the object at different orientations; and analyzing the echoes from all directions to produce an image of the region of the object. The aperture of the transducer generating the beam is at least substantially equal to the aperture generated by a linear array of transducer elements extending across the substantially shortest distance between two opposite edges on the two-dimensional array. The ultrasound power emitted from the transducer elements is not spatially uniform, and the multiple echoes reduce speckle in the image.

8 Claims, 2 Drawing Sheets

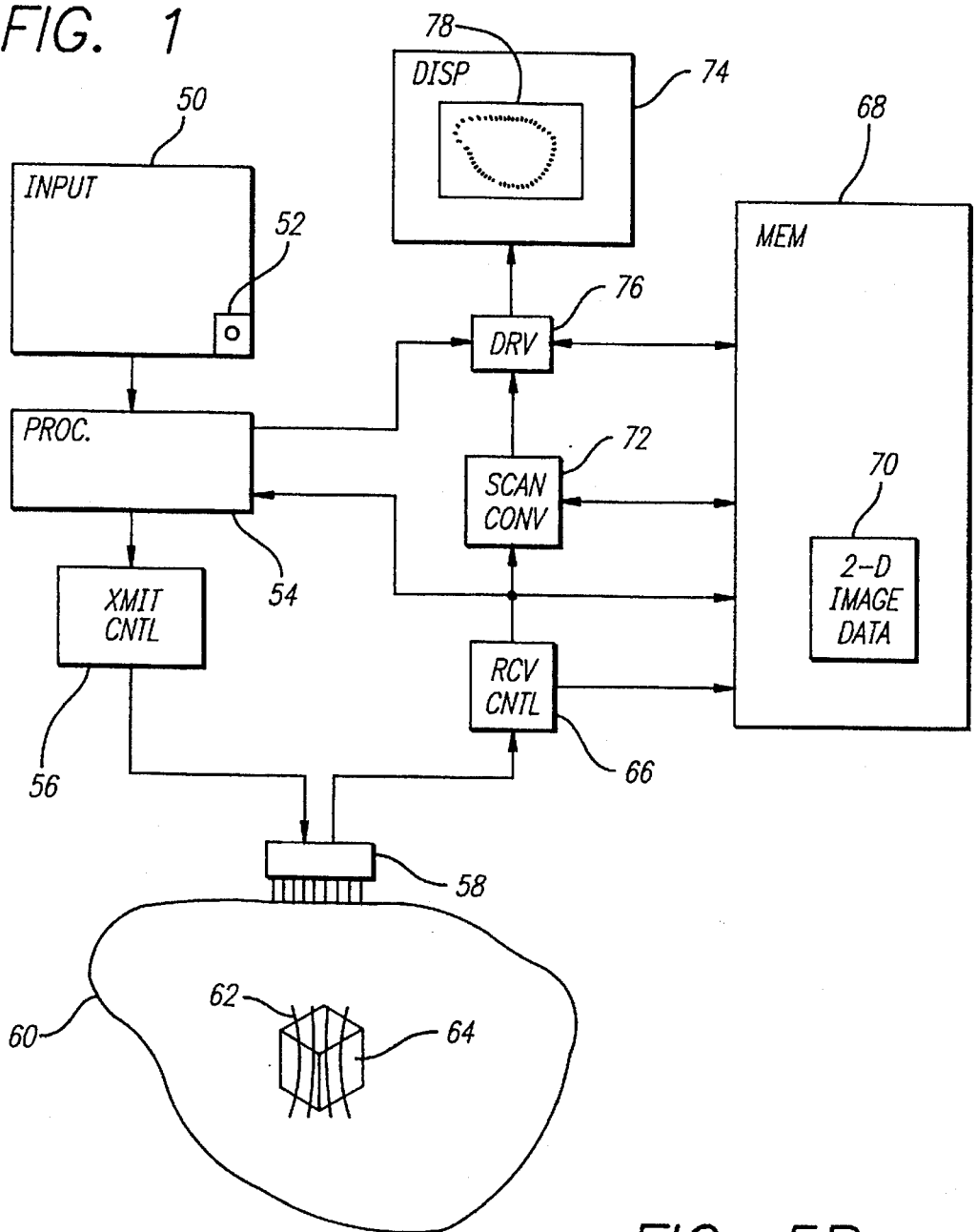
FIG. 1
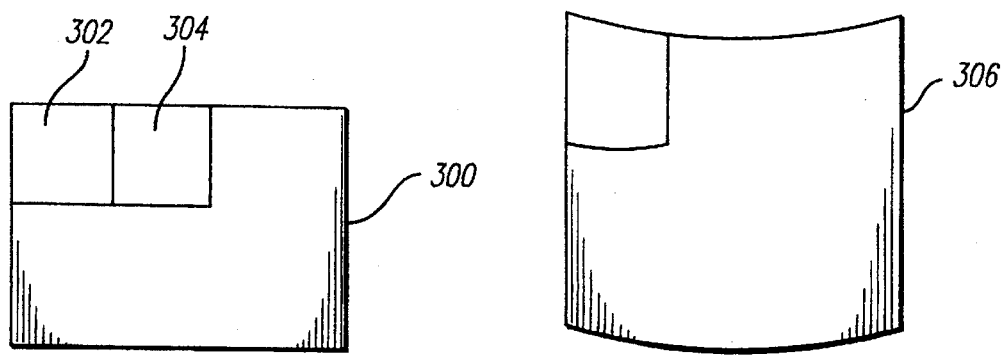
FIG. 5A
FIG. 5B

SPECKLE REDUCTION IN ULTRASOUND IMAGING

BACKGROUND OF THE INVENTION

1. Field of the Invention

The present invention relates generally to ultrasound imaging and more particularly to speckle reduction in ultrasound imaging.

2. Description of the Related Art

Ultrasonic imaging has become one of the most important and popular diagnostic tools, with a wide range of applications. Particularly due to its non-invasive and non-destructive nature, ultrasound imaging has been extensively used by the medical profession.

One fundamental problem in all types of imaging is noise from backscattered signals, which obscures the details of the target image or echo. One type of noise, commonly known as "speckle" in tissue characterization and optics, results from, constructive and destructive interference, and appears as a random mottle superimposed on the image. Normally, speckle is from objects whose dimensions are smaller than the wavelengths of the radiation source, making it impossible to eliminate the speckle simply by increasing the resolution of the imaging device. Moreover, speckle is from objects that are stationary and randomly distributed. Since the speckle has no phase or amplitude variation as a function of time, one cannot suppress it by averaging the imaging signals in time. In other words, speckle signals are coherent, and cannot be reduced through averaging.

One method to reduce speckle is through a method known as spatial diversity or spatial compounding. The idea is to capture the target image a number of times with the radiation illuminating the target from different directions. The multiple images are then combined to remove the speckle. The success of the method is a result of the statistical independence of speckle patterns, and the fact that the target size is much larger than the speckle-causing scatterers. By taking images from a number of directions, the speckle is made to behave like uncorrelated time-varying noise, while the target echoes remain correlated and virtually unchanged. With a number of those images combined together through spatial compounding, speckle can be reduced. The calculations to combine images formed from different directions for reducing speckle are well known.

Typically, the way to generate multiple images from different directions is to excite different sections of a linear array of piezo-electric sources/detectors or transducer elements, which generate and measure the ultrasound. For example, one can separate a linear array of 128 transducer elements into 4 successive sections, each section with 32 elements. The sections are excited one at a time, with the ultrasound beam from each section steered so that all four beams are focused at substantially the same region, but from different directions. Typically, steering of a beam is done through controlling the delays of the signals from a number of transducer elements; such techniques are well-known to those skilled in the art. Speckle can then be reduced by combining the four echoes from the four different directions. The problem with this method is related to the aperture size of the array, which is defined as the area where the transducer elements are activated to generate the beam. Instead of using the entire array, one can only use a part of the array at one time, which significantly reduces the aperture size of the array, and the lateral resolution of the images formed. Also the reduced aperture size would significantly reduce the signal strength for imaging and decrease the signal-to-noise ratio of the images formed.

A paper, titled, "Speckle Reduction in Pulse-Echo Ultrasonic Imaging Using a Two-Dimensional Receiving Array," written by Giesey et al., and published in IEEE Transaction on Ultrasonics, Ferroelectrics and Frequency Control, Vol. 39, No. 2, March 1992, describes a two-dimensional transducer to reduce speckle. In that paper, the transducer includes a center disk of transducer elements, which are surrounded by eight concentric annular arrays or annuli of transducer elements, with each annulus having a different radius. Each annulus is divided into eight equal segments, creating a total of sixty-four separate segments. In operation, the center disk would generate an ultrasound pulse, and then different segments would capture the echo from the pulse to generate an image of the region interrogated. With different segments capturing the echo from different directions, Giesey can again reduce the speckle in the image. However, similar to the one-dimensional array, Giesey has to trade-off lateral resolution or aperture size—using segments—to reduce speckle.

From the above discussion, it should be apparent that there is a need to reduce speckle Without requiring significant trade-offs. In other words, one would like to reduce speckle, without significantly reducing the aperture size of the transducer, or the lateral resolution of the images formed.

SUMMARY OF THE INVENTION

The present invention reduces speckle in ultrasound imaging without reducing the lateral resolution of the images formed. The invented method is based on a system that includes a transducer with a two-dimensional array of transducer elements to generate an ultrasound beam, and to illuminate substantially the same region of an object with the beam at a number of orientations. The echo generated with the beam at each orientation is captured, and all the echoes are analyzed to produce an image of the region of the object. Since beams from different orientations illuminating the object are independent of each other, the independent echoes can be mathematically combined to reduce speckle in the image. As compared to a one-dimensional array, the two-dimensional array provides another degree of freedom. The second degree of freedom allows one to change the orientations of the beam illuminating the object, which, in turn, generates independent echoes to reduce speckle in the image of the object.

The second degree of freedom, based on the present invention, also allows the aperture of the transducer generating the beam at various orientations to be at least substantially equal to the aperture that is generated by a linear array of transducer elements, extending across the substantially shortest distance between two opposite edges on the two-dimensional array. Thus, the aperture size of a linear array is maintained while speckle in the image is reduced, and no trade-off is needed.

In order to create beams with different orientations, in the present invention, the ultrasound power emitted from the transducer elements is not uniform. In other words, the apodization function, which defines the amount of power emitted from each transducer element to generate an ultrasound beam, is not a constant.

In one preferred embodiment, the apodization function is in the shape of a ridge, and the beam is electronically controlled to rotate substantially about the center of the two dimensional array to illuminate—that is, to insonify—substantially the same region of the object.

In another preferred embodiment, the two-dimensional array is a part of a larger two-dimensional array, which has many smaller two-dimensional arrays. Each of the smaller two-dimensional arrays is electronically controlled as in one of the above preferred embodiments to generate a beam to illuminate the object.

BRIEF DESCRIPTION OF THE DRAWINGS

FIG. 1 shows the main components in an ultrasonic imaging machine, which incorporates the invention.

FIGS. 5A–B show large two-dimensional arrays incorporating a number of the two-dimensional arrays in the present invention.

Same numerals in FIGS. 1–5 are assigned to similar elements in all the figures. Embodiments of the invention are discussed below with reference to FIGS. 1–5.

DETAILED DESCRIPTION

Figure 2:
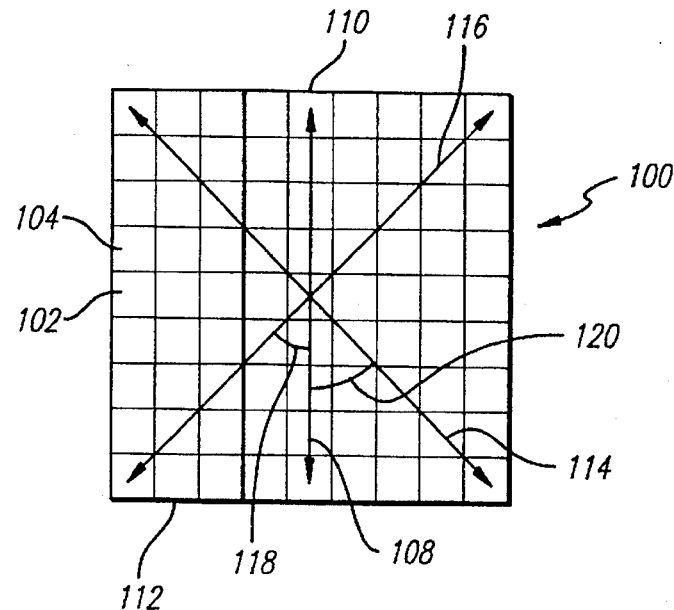
FIG. 2 shows a representation of a two-dimensional array in the invention.

FIG. 1 illustrates some of the main components of an ultrasonic imaging system according to the invention. The user enters various conventional scan parameters into an input unit 50, which typically includes such devices as a keyboard, knobs, and buttons, and a cursor-control device such as a trackball 52 or mouse. The input unit is connected to a processing system 54, which will typically be an electrically connected and cooperating group of processors such as microprocessors, digital signal processors, and application-specific integrated circuits (ASIC's); the processing system may, however, also be implemented by a single processor as long as it is fast enough to handle the various tasks described below.

The processing system 54 sets, adjusts, and monitors the operating parameters of a conventional transmission control circuit 56, which generates and applies electrical control and driving signals to an ultrasonic probe 58, which includes a transducer with an array of piezo-electric transducer elements. The transducer elements generate ultrasonic waves, typically in the form of pulses, when electrical signals of the proper voltage and frequency are applied to them.

With the probe 58 placed against the body of a patient, these ultrasonic waves enter a portion 60 of the patient's body. By varying the phasing, amplitude, and timing of the driving signals, the ultrasonic waves are focused to form scan beams 62 that typically fan out from the probe. A few such beams are shown in FIG. 1. A region of interest, that is, the region that the user wants to have an image of, is shown as an interrogation region or volume 64. The manner in which ultrasonic scanning signals are applied to a patient's body is well understood in the art and is therefore not described further.

Ultrasonic echoes from the waves transmitted into the body return to the array in the probe 58. As is well understood, the transducer elements thereby convert the small mechanical vibrations caused by the echoes into corresponding electrical signals. Amplification and other conventional signal conditioning is then applied to the return signals by a reception controller 66. This processing includes, as needed, such known signal-conditioning as time-gating, gain compensation, and noise filtering, in order to identify the echo signals that correspond to the interrogation region 64.

The reception controller 66, all or a part of which is normally integrated into the processing system 54 itself, processes the ultrasonic, radio-frequency (RF) echo signals from the transducer (typically on the order of a few to tens of megahertz) to form reception beams along the transmission beam direction. This is well known in the art of ultrasonic imaging. The magnitude values of the received beams for the two-dimensional interrogation region are stored digitally in a memory 68 as 2-D frame data 70. Each set of frame data corresponds to one image frame, that is, to a 2-D cross section of the interrogation region.

The stored data format is normally not in the same shape or size as what the user wants to see displayed. The echo magnitude values for an image frame are therefore applied to a conventional scan converter 72, which converts the stored image into a display format that is suitable for use in driving a display device 74. The display device 74 typically includes a conventional display driver 76 and a screen 78, such as an LED display or a CRT, that is divided into an X-Y (or polar) matrix or pattern of picture elements or "pixels" that make up an image that the user can view and interpret.

The image is displayed as a pattern of image elements that correspond to the received echo magnitude from corresponding portions of one 2-D frame of data from the interrogation region. Note that a displayed image element will often be made up of more than one pixel, but that this depends on the relative resolutions of the scan and of the display, which are not of particular importance to the present invention.

FIG. 2 shows a representation of a transducer 100 in the ultrasound probe 58 according to the invention. The transducer includes many ultrasound transducer elements, such as 102 and 104, integrated to form a two-dimensional array of transducer elements. In the representation, the transducer is a square array. However, other configurations, such as a circular or a rectangular array, are also applicable. The transducer generates the ultrasound scan beams.

Figure 3:
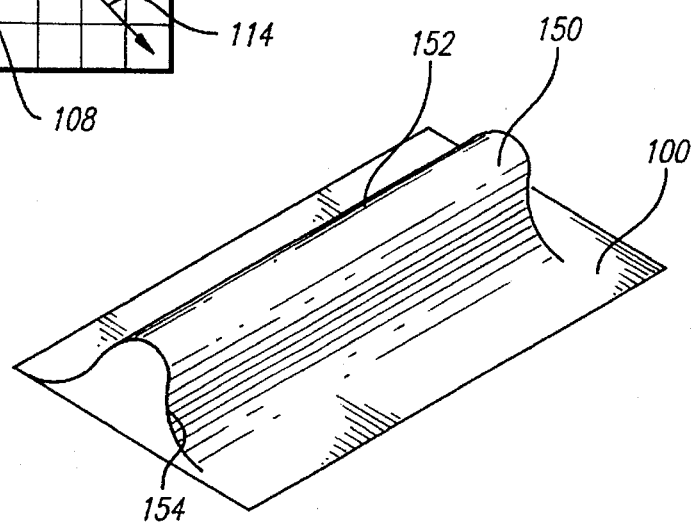
FIG. 3 shows an apodization function with one dimension being in the shape of a ridge, generated by a two-dimensional array of the present invention.

FIG. 3 shows one preferred apodization function or power profile 150 for the ultrasound beam. As shown by the profile, the ultrasound power emitted from the transducer elements is not spatially uniform; in other words, the apodization function is not a constant. In the example shown, the power profile is in the shape of a ridge 152 in one dimension, and in the shape of a Gaussian profile 154 in another dimension. Other profiles may, however, be used. In other preferred embodiments, for example, the profile may be in the shape of multiple ridges in one dimension, or the function may have the shape of a Hamming profile in the other direction, or both. Whether the profile has a ridge or a Gaussian profile is not crucial, as long as the analysis of the echoes generated by the beams takes into account the beam profile. Typically, a linear set of transducer elements operating at maximum power generates the ridge, and the transducer elements around the linear set operate at reduced power. In FIG. 2, a linear array of transducer elements 108 is represented by a line with arrows at both ends. The methods for generating such profiles are well known.

In one preferred embodiment, the aperture of the transducer generating the beam is at least substantially equal to the aperture generated by a linear array of transducer elements extending across the substantially shortest distance between two opposite edges, such as 110 and 112, of the two-dimensional array 100. This can be achieved by activating the linear array 108 at maximum power, and those around it at reduced power, so as to generate the power profile shown in FIG. 3. If the two-dimensional array is rectangular in shape, the opposite edges selected would again be those for which the distance across them is the shortest. If the array is circular, the shortest distance is preferably the diameter of the circle.

Figure 4:
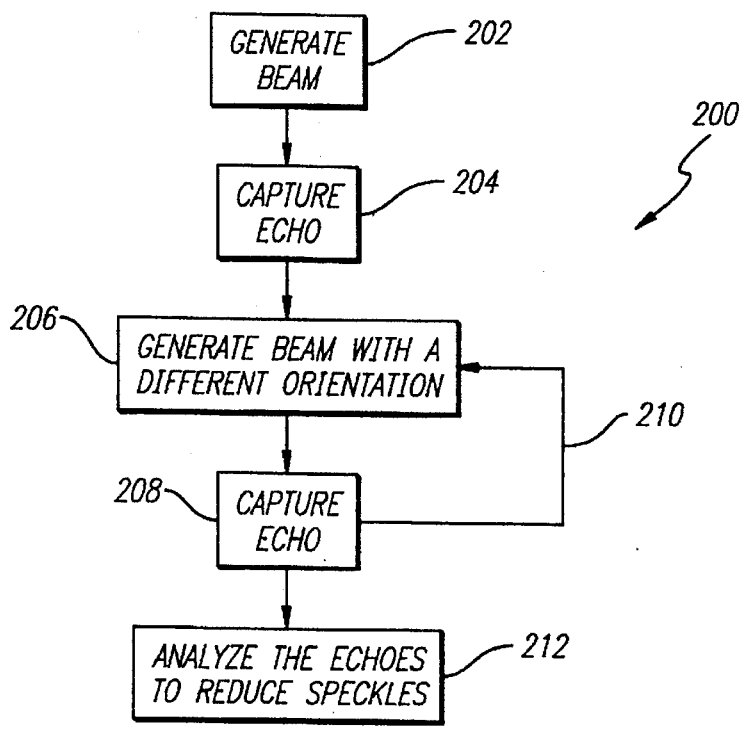
FIG. 4 shows a set of preferred steps for the present invention.

FIG. 4 shows preferred steps 200 to reduce speckle in the present invention. Transducer elements on the two-dimensional array 100 are activated to generate 202 an ultrasound beam, whose orientation can be electronically controlled. Typically, the beam is activated as a pulse. After generating the pulse, the transducer elements capture 204 the echo reflected from the interrogation volume 64 and its surroundings, which are insonified by the beam. Then the transducer generates 206 a second ultrasound beam with an orientation that is different from the orientation of the previously generated ultrasound beam. The second beam illuminates substantially the same region as the first-generated beam. This illumination generates another echo, which is captured 208 by the transducer. The step of generating beam 206 and capturing echo 208 can be repeated 210 for a desired number of times to generate many echoes, with each generated beam at an orientation that is different from all the other generated beams to illuminate substantially the same region. All the echoes are analyzed 212 to produce an image of the interrogation region. Based on the multiple independent echoes, speckle in the image is reduced.

One preferred method to change the orientation of the beam is to rotate the beam substantially about the center of the two dimensional array to illuminate substantially the same interrogation region 64. In one preferred embodiment, different transducer elements are activated at different times to rotate the beam. For example, the linear array (which is a sub-array of the 2-D array 100) that operates at full power changes from 108 to 114 to 116 at different time, with transducer elements around them going down in power to produce the beam profile as in FIG. 3. Based on this method, different rotational positions are determined. Typically, at each position, ultrasound pulses are generated, and the transducer would change from a transmitting to a receiving mode to capture echoes reflected by the interrogation region and its surroundings. In one preferred embodiment, the angles between selected adjacent positions, such as 118 and 120, are substantially the same. In another embodiment, the angles are not constant, so as to create additional randomness in the echoes captured. It is also possible to orient the various beams with random relative angular positions.

In yet another preferred embodiment, the delays of the signals from the transducer elements generating the ridge are controlled to steer the beam to illuminate different regions in space. Steering the transmit beam, applying the appropriate apodization function to the transducer elements according to the invention, and sensing the return echo signals, are carried out under the control of the transmission control circuit 56 and the reception controller 66, which may either have the appropriate parameters in internal memory or other circuitry, or may down-load them from the processor 54. By steering the beam, one can image different interrogation regions.

There are at least two preferred ways to generate images of different interrogation regions with the transducer, and in both ways, the steps in FIG. 4 are repeated. The first preferred way to repeat the steps is to generate at least two different orientation beams, and then steer the beam to illuminate another region and generate the different orientation beams again. The second preferred way to repeat the steps is to steer the generated beam to illuminate many regions, and then change the beam orientation, and steer the beam to illuminate the same regions again. In the first preferred way, all the steps in FIG. 4 are implemented before the beam is steered and before all the steps in FIG. 4 are implemented again. In the second preferred way, the step of delay change is embedded within the steps in FIG. 4. For example, the beam generation step 202 and the beam-capture step 204 are repeated many times, wherein for each time, the delays of the beams are controlled to illuminate a different region. Then the steps 206 and 208 are repeated, with the delays of the beams controlled to illuminate the different regions again. Finally, at step 212, all the echoes from each region are separately analyzed to reduce speckle in the image from each region. Such steering techniques should be obvious to those skilled in the art, and will therefore not be described further.

Imaging can also be done in parallel. For example, one apodization function has three parallel ridges generating three beams. The three beams typically are steered to illuminate different directions, with the aperture generating each beam being at least substantially equal to the aperture generated by a linear array of transducer elements that extends across the substantially shortest distance between two opposite edges on the two-dimensional array. If the transducer is circular, in one embodiment, there will be three linear arrays of transducer elements operating at full power, with elements operating around them at reduced power. One linear array goes through the center of the transducer, and the other two are closely adjacent to that array. The three beams can operate in parallel, such as rotating together around the transducer, and capturing echoes along the way.

FIG. 5A shows a number of the two-dimension arrays of the present invention, such as 302 and 304, combined to form a large two-dimensional array, such as 300, in the ultrasound probe 58. The large array generates a number of ultrasound images for different interrogation regions. Each image is generated by a small two-dimensional array by one of the inventive methods described above. The images can be generated simultaneously or sequentially or in a staggered manner, where one array is activated before another array terminates its measurement. With the numerous small arrays interrogating different regions, one may not need to steer the beams from each array to interrogate different regions in the object 60.

The large two-dimensional array can be substantially flat as shown in FIG. 5A, or the large two-dimensional array 306 can be curved as shown in FIG. 5B, where the curvature shown is only in one dimension. However, the curvature can be in two dimensions, as in a hemispherical surface. The way to produce a flat or a curved two-dimensional array is known.

Note that one advantage of the invention is that it is possible to achieve different beam orientations, or different orientations for the substantially linear region of maximum transducer element power, without the operator having to move the probe physically.

I claim:

1. A method for generating an ultrasound image of a region in an object using a transducer with a two-dimensional array of transducer elements, the method comprising the steps of:

selecting an aperture formed by the transducer elements such that the aperture is at least substantially equal to the aperture generated by a linear array of transducer elements extending across the substantially shortest distance between two opposite edges on the two-dimensional array, generating a first ultrasound beam by controlling the driving signal to the transducer elements so that the power emitted by the elements forms a peak power profile that substantially extends across the first aperture with a first substantially linear orientation with respect to one of the dimensions of the two-dimensional array, sensing the echo generated from the first beam insonifying the region of the object, generating a second ultrasound beam by controlling the driving signals to the transducer elements so that the power emitted by the elements forms a peak power profile with a second substantially linear orientation with respect to one of the dimensions of the two-dimensional array that is different from the first orientation, sensing the echo generated from the second beam insonifying substantially the same region as the first beam, repeating said generating and sensing steps to provide additional echoes, and analyzing the sensed echoes to produce an image of the region of the object with reduced speckle.

2. A method as recited in claim 1 further comprising the steps of generating and sensing the return echo signals from additional ultrasound beams insonifying substantially the same region of the object, each beam having an orientation different from the first and second orientations and from the orientations of other of said additional beams.

3. A method as recited in claim 1, wherein said generating steps comprise generating said beams such that the beam orientations are displaced rotationally relative to each other about a central portion of the two-dimensional array.

4. A method as recited in claim 1, wherein said generating step comprises generating each beam according to a two-dimension apodization function that has a substantially linear region of maximum amplitude.

5. A method as recited in claim 4, wherein in said generating steps the orientation of each beam is defined by the corresponding linear region of maximum amplitude and the beam orientations are such that the beams are displaced rotationally relative to each other about a central portion of the two-dimensional array.

6. A method as recited in claim 1, furthering including the following steps:

activating the plurality of transducer elements with a delay argument;

steering the beams by adjusting the delay argument to insonify a plurality of regions of the object; and for each region, repeating the steps of generating ultrasound beams with respective orientations, and sensing and analyzing the corresponding echoes.

7. A method for generating an ultrasound image using a plurality of two-dimensional arrays as recited in claim 1, such that the plurality of two-dimensional arrays are grouped together to form a large two-dimensional array.

8. A system for generating an ultrasound image of an object, comprising:

a transducer with a two-dimensional array of transducer elements for insonifying a region of the object, means for selecting an aperture formed by the transducer elements such that the aperture is at least substantially equal to the aperture generated by a linear array of transducer elements extending across the substantially shortest distance between two opposite edges on the two-dimensional array, means for generating a first ultrasound beam by controlling the driving signal to the transducer elements so that the power emitted by the elements forms a peak power profile that substantially extends across the first aperture with a first substantially linear orientation with respect to one of the dimensions of the two-dimensional array, means for sensing the echo generated from the first beam insonifying the region of the object, said generating means for further generating a second ultrasound beam by controlling the driving signals to the transducer elements so that the power emitted by the elements forms a peak power profile with a second substantially linear orientation with respect to one of the dimensions of the two-dimensional array that is different from the first orientation, said sensing means for further sensing the echo generated from the second beam insonifying substantially the same region as the first beam, means for controlling said generating and sensing means for repeating said generating and sensing to provide additional echoes, and means for analyzing the sensed echoes to produce an image of the region of the object with reduced speckle.

* * * * *